(12) United States Patent
Wruck et al.

(10) Patent No.: US 8,267,087 B2
(45) Date of Patent: Sep. 18, 2012

(54) DEVICE FOR ADSORBING AND DESORBING ANESTHETIC

(75) Inventors: Norbert Wruck, Lübeck (DE); Götz Kullik, Lübeck (DE); Michael Riecke, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1042 days.

(21) Appl. No.: 12/208,575

(22) Filed: Sep. 11, 2008

(65) Prior Publication Data

US 2009/0095295 A1   Apr. 16, 2009

(30) Foreign Application Priority Data

Oct. 11, 2007   (DE) .......................... 10 2007 048 893

(51) Int. Cl.
*A62B 7/10* (2006.01)
*A62B 18/00* (2006.01)

(52) U.S. Cl. ............................. 128/205.27; 128/200.24

(58) Field of Classification Search ............ 128/204.18, 128/204.21, 205.27–205.29; 96/125, 111, 96/143, 146
See application file for complete search history.

(56) References Cited

U.S. PATENT DOCUMENTS

| | | | |
|---|---|---|---|
| 4,015,599 A | 4/1977 | Peterson | |
| 5,471,971 A | 12/1995 | Suzuki et al. | |
| 5,471,979 A | 12/1995 | Psaros et al. | |
| 5,515,845 A * | 5/1996 | Filipovic et al. | 128/205.12 |
| 6,488,028 B1 * | 12/2002 | Lambert | 128/205.12 |
| 7,077,134 B2 * | 7/2006 | Ahlmen | 128/205.12 |
| 2003/0106429 A1 * | 6/2003 | Wang et al. | 95/90 |
| 2004/0103894 A1 * | 6/2004 | Loncar | 128/203.12 |
| 2007/0062535 A1 * | 3/2007 | Psaros | 128/205.28 |
| 2009/0165800 A1 * | 7/2009 | Broborg | 128/205.12 |

FOREIGN PATENT DOCUMENTS

| | | |
|---|---|---|
| EP | 1 222 940 A2 | 7/2002 |
| EP | 1 440 704 B1 | 7/2004 |
| WO | WO 03 090826 A1 | 11/2003 |
| WO | 2005/037357 A1 | 4/2005 |
| WO | 2006/046908 A1 | 5/2006 |

\* cited by examiner

*Primary Examiner* — Steven Douglas
*Assistant Examiner* — Rachel Young
(74) *Attorney, Agent, or Firm* — McGlew and Tuttle, P.C.

(57) ABSTRACT

A device is provided for adsorbing and desorbing anesthetic has good control of anesthetic dispensing such as in an anesthetic system. An adsorption filter is provided with adsorption beds (13, 14), which can be pivoted between an inspiration line (4) and an expiration line (6). The anesthetic is dispensed in the expiration line (6) on the incoming flow side of the adsorption bed (14) arranged there.

20 Claims, 3 Drawing Sheets

DEVICE FOR ADSORBING AND DESORBING ANESTHETIC

CROSS REFERENCE TO RELATED APPLICATIONS

This application claims the benefit of priority under 35 U.S.C. §119 of German Patent Application DE 10 2007 048 893.0 filed Oct. 11, 2007, the entire contents of which are incorporated herein by reference.

FIELD OF THE INVENTION

The present invention pertains to a device for adsorbing and desorbing anesthetic.

BACKGROUND OF THE INVENTION

Devices for the recycling of expired anesthetic are known from the state of the art and are based on the principle that expired gas is sent over a filter, which adsorbs expired anesthetic and fresh breathing gas is subsequently sent over the filter during a desorption phase in order to enrich it with anesthetic. In addition to the anesthetic adsorber, a carbon dioxide absorber may be present, which adsorbs the carbon dioxide expired by the patient.

In a device known from U.S. Pat. No. 5,471,971, a gas duct, which is common in some sections, is provided for the inspiration and the expiration, in which the adsorption filter for anesthetic is arranged. In addition, a carbon dioxide absorber, which retains carbon dioxide that may be present in the gas to be breathed in, is located in an inspiration branch arranged downstream of the adsorption filter. The anesthetic is added directly in the vicinity of the patient tube.

The drawback of the prior-art device is that the adsorption filter for anesthetic is arranged in a common gas duct, through which gas to be inspired and gas to be expired flow, and the additional carbon dioxide absorber is therefore needed to remove carbon dioxide from the gas to be inspired.

A device for the recycling of anesthetic, in which an adsorption filter is moved between two gas ducts in order to expose an equal section of the filter alternatingly to the interior space of each channel, is known from EP 1 440 704 B1. Since separate channels are present for the gas to be inspired and the expired gas in this device, the dead space volume decreases to the volume of the filter sections that are pivoted between the gas ducts. However, more specific data on how the anesthetic is supplied to the patient cannot be found in the document. A drawback of the prior-art device is also that a rinsing gas is needed during a rapid termination phase to rinse through the adsorption bed and to remove the anesthetic.

SUMMARY OF THE INVENTION

The basic object of the present invention is to improve a device for recycling anesthetic in respect to good control of the anesthetic dispensing and as part of an anesthetic system.

According to the invention, a device is provided for adsorbing and desorbing anesthetic. The device comprises an adsorption filter with at least one first adsorption bed and a second adsorption bed as well as an inspiration line and an expiration line between a respirator (also known as a ventilator) and a patient. The inspiration line and the expiration line send breathing gas through one of the adsorption beds. A pivoting means is provided for exposing the first adsorption bed and the second adsorption bed alternatingly to the inspiration line and to the expiration line. An anesthetic dispenser is provided for releasing anesthetic onto the adsorption bed during the period of adsorption.

The advantage of the device described according to the present invention is a more uniform release of anesthetic to the breathing gas with the involvement of anesthetic dispensers operated according to different principles of action. As a result, a broad range of use is obtained, and dispensing of all commercially available anesthetics becomes possible. The anesthetic is advantageously supplied into the breathing gas within the expiration line on the incoming flow side of the adsorption bed arranged there. Introducing the anesthetic directly into the adsorption bed in order for the anesthetic to be adsorbed by this over its entire surface is also within the scope of the present invention. The anesthetic can now become distributed uniformly within the adsorption bed arranged there during the period before the desorption phase before it is then supplied again into the gas to be inspired during the next inspiration stroke. If liquid anesthetic is being dispensed, this can evaporate directly in the expiration line in case of small volumes, or a separate evaporator may be provided there.

It is especially advantageous to provide the adsorption filter, in addition to the adsorption beds, with at least one or even more empty sectors. The adsorption filter is advantageously designed in this case in the form of a filter wheel and it advantageously contains four adsorption beds and two empty sectors. The empty sectors have neither adsorption nor desorption properties and are used to lower the anesthetic concentration in a short time in order for the patient's anesthesia to be able to be terminated. The empty sectors are advantageously arranged on the filter wheel such that they can be pivoted simultaneously both into the inspiration line and into the expiration line.

To improve the desorption properties of the adsorption beds, it is advantageous to provide a heating device in the area of the adsorption filter. This heating device is advantageously designed as an infrared radiator or a ultraviolet (UV) radiator.

The anesthetic concentration is advantageously monitored either in the inspiration line or in the expiration line or directly in the area of the patient port. Measuring systems that directly detect the anesthetic concentration may be used for this, or suction type measuring systems, which take a gas sample to be analyzed from the breathing gas, are used.

Anesthetic dispensers, which release either liquid anesthetic or gaseous anesthetic, may be used in the device described according to the present invention. It is also possible in case of dispensing gaseous anesthetic to feed saturated anesthetic vapor directly into the expiration line.

If an anesthetic measuring device operating by suction is used, a commercially available anesthetic evaporator, which contains as the fresh gas the breathing gas drawn off from the anesthetic measuring device, can be advantageously used. This breathing gas is enriched with anesthetic within the anesthetic evaporator and is then supplied again into the breathing gas on the incoming flow side of the adsorption bed arranged in the expiration line. A loss of breathing gas due to the suction type measurement is avoided as a result. An especially high efficiency can be attained with this type of anesthetic dispensing.

The anesthetic being stored in the expiration line by the adsorption bed arranged therein must again be supplied into the gas to be breathed in during the inspiration phase. A pivoting means, which pivots the adsorption beds of the adsorption filter between the inspiration line and the expiration line, is provided for this. The pivoting may also take place by oscillation, or it is carried out in the form of a pure rotary motion, in which case additional adsorption beds may also be present for this on the adsorption filter. Adaptation of the switchover to the phases of breathing can be achieved by means of a signal line, which establishes a data connection between the pivoting means and the connected respirator. The switchover is preferably carried out each time after a full breathing phase. In the simplest case, the pivoting means is a motor, which is connected to the adsorption filter.

If there is no possibility of synchronization with the respirator, a breathing phase detector, which is designed to generate switchover signals for the pivoting means, may be arranged directly in the inspiration line or in the expiration line.

It is especially advantageous to use the anesthetic measuring device, which detects the inspired and expired anesthetic concentration and also the carbon dioxide concentration, directly for detecting the breathing phase. Breathing phase detection is possible by the evaluation of the course of the carbon dioxide concentration in the breathing gas.

The anesthetic measuring device, the anesthetic dispenser and a regulator are advantageously connected together in the form of a control circuit in order to set a predetermined anesthetic concentration in the breathing gas. A certain anesthetic concentration is preset by means of a set point adjuster, and the actual value is detected in the vicinity of the patient by the anesthetic measuring device. Since the anesthetic is supplied into the breathing gas via the adsorption bed arranged in the expiration line, possible overshooting in the control circuit is suppressed, because a sufficient intermediate storage capacity is present in the adsorption bed for compensating deviations. To increase the concentration at the patient rapidly, it is advantageous to switch over the outlet of the anesthetic dispenser to the inspiration line at least temporarily. Build-up of a high anesthetic concentration is thus achieved in the inspired gas, which is not affected by the adsorption beds.

To condition the breathing gas, a heat and moisture exchanger is provided in the vicinity of the patient. This heat and moisture exchanger stores the moisture released during expiration and returns this into the gas to be inspired during the next phase of inspiration. Should the moisture content thus attained in the breathing gas not be sufficient, a humidifier, which sets a sufficient moisture level in the breathing gas, may be additionally provided in a stub line leading to the patient.

An exemplary embodiment of the present invention is shown in the drawings and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
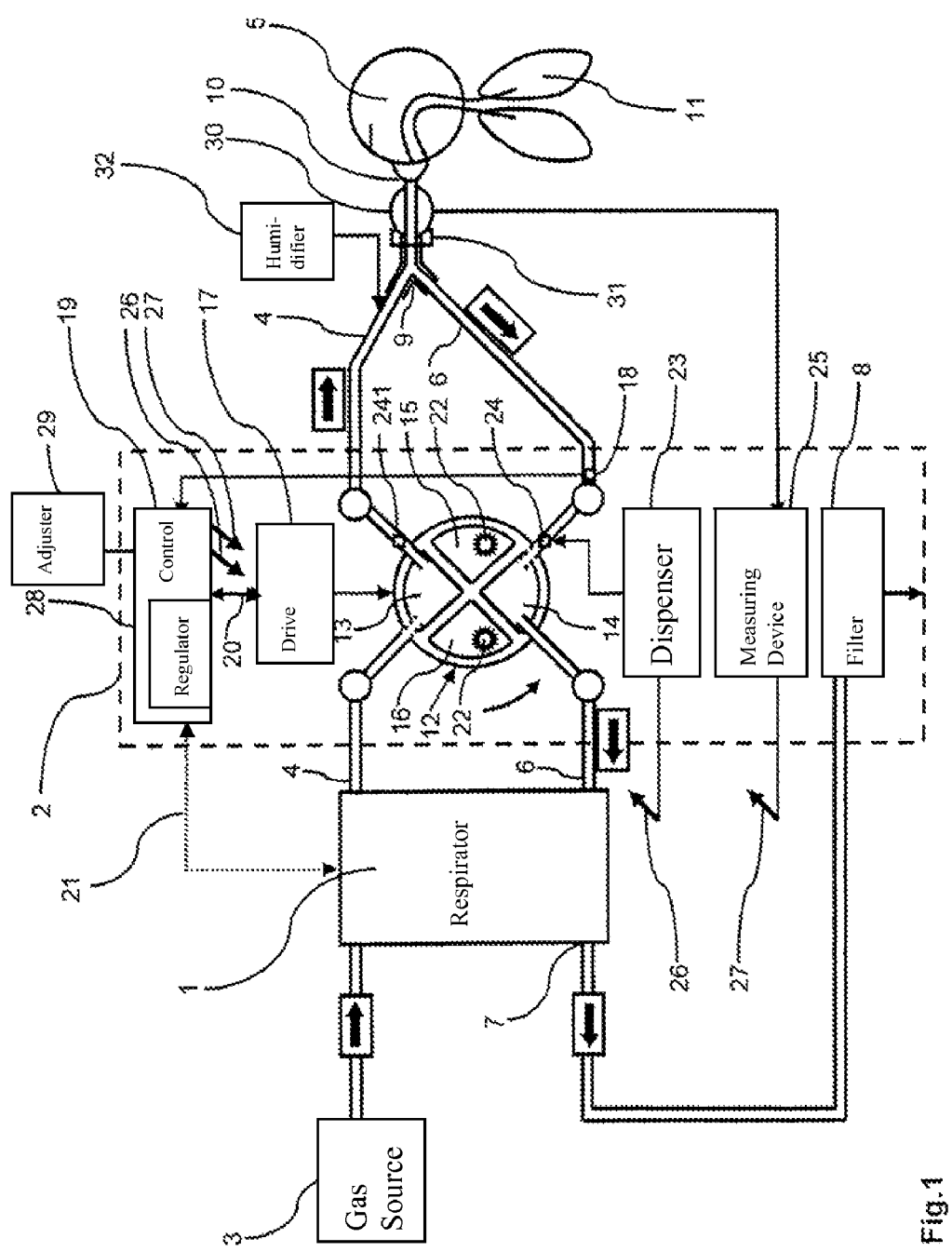
FIG. 1 is a schematic view showing a respirator combined with an anesthetic module.

Referring to the drawings in particular, FIG. 1 schematically illustrates a respirator 1 combined with a gaseous anesthetic module 2 for adsorbing and desorbing anesthetic. The respirator 1 contains fresh breathing gas from one or more pressurized gas sources 3. The gas to be inspired reaches a patient 5 via an inspiration line 4 and the gaseous anesthetic module 2. The expired gas flows back into the respirator 1 through an expiration line 6 and the gaseous anesthetic module 2. A breathing gas outlet 7 on the respirator 1 is connected to an adsorption filter 8, which retains anesthetic residues.

The inspiration line 4 and the expiration line 6 are connected to one another via a Y-piece 9 in the area of the patient 5, and a breathing tube 10 at the Y-piece 9 establishes the flow connection to the patient's lungs 11. Air, optionally also with added oxygen, is used as breathing gas.

The gaseous anesthetic module 2 contains a rotary filter wheel 12 with four adsorption beds 13, 14, 15, 16, through which either gas to be inspired flows alternatingly during a desorption phase or which is exposed to the expired gas during an adsorption phase. The filter wheel 12 is arranged such that a first adsorption bed 13 is arranged within the inspiration line 4 and gas to be inspired flows through it, and a second adsorption bed 14 located opposite the first adsorption bed 13 is in the path of flow of the expiration line 6. The anesthetic being stored in the first adsorption bed 13 is released during the inspiration phase onto the gas to be inspired, while the anesthetic is stored in the second adsorption bed 14 during expiration. Anesthetic residues possibly left behind in the expired gas are retained in the adsorption filter 8 arranged downstream of the breathing gas outlet 7.

The filter wheel 12 is connected to a drive 17, which pivots the adsorption bed loaded with anesthetic into the area of the inspiration line 4 at the end of the expiration phase.

A breathing phase detector 18 connected to the expiration line 6 is connected to a control unit 19, which generates switchover signals for the drive 17. The control unit 19 is connected via a bidirectional data line 20 to the drive 17, and the synchronization between the control unit 19 and the respirator 1 takes place via a signal line 21. UV radiators 22 are arranged in the area of the adsorption beds 15, 16 in order to improve the desorption capacity thereof.

An anesthetic dispenser 23 feeds either liquid anesthetic or a saturated anesthetic vapor into an anesthetic port 24 arranged on the incoming flow side of the second adsorption bed 14. The anesthetic port 24 may also be arranged directly within the second adsorption bed 14, so that the anesthetic is distributed uniformly over the second adsorption bed 14. To build up the anesthetic in the inspiration line 4 rapidly, the anesthetic may also be mixed briefly with the breathing gas via an alternative anesthetic port 241 in the inspiration line 4. A gaseous anesthetic sensor 30 arranged between the Y-piece 9 and the tube 10 is connected to an anesthetic measuring device 25 and detects the anesthetic concentrations in the gas to be breathed in and the expired gas. The anesthetic measuring device 25 and the anesthetic dispenser 23 are connected to the control unit 19 via signal lines 26, 27. The control unit 19 contains a regulator 28, which is in functional connection with a set point adjuster 29 for the anesthetic concentration, the anesthetic dispenser 22 as a final control element and the anesthetic measuring device 25 as an actual value transducer. A control circuit for setting an anesthetic concentration preset by the set point adjuster 29 is formed by the regulator 28, the anesthetic dispenser 23 and the anesthetic measuring device 25 with the anesthetic gas sensor 30.

A heat and moisture exchanger 31 is provided at the Y-piece 9 to condition the breathing gas. In addition, the gas to be inspired may also be humidified with an optional humidifier 32 if needed.

Figure 2:
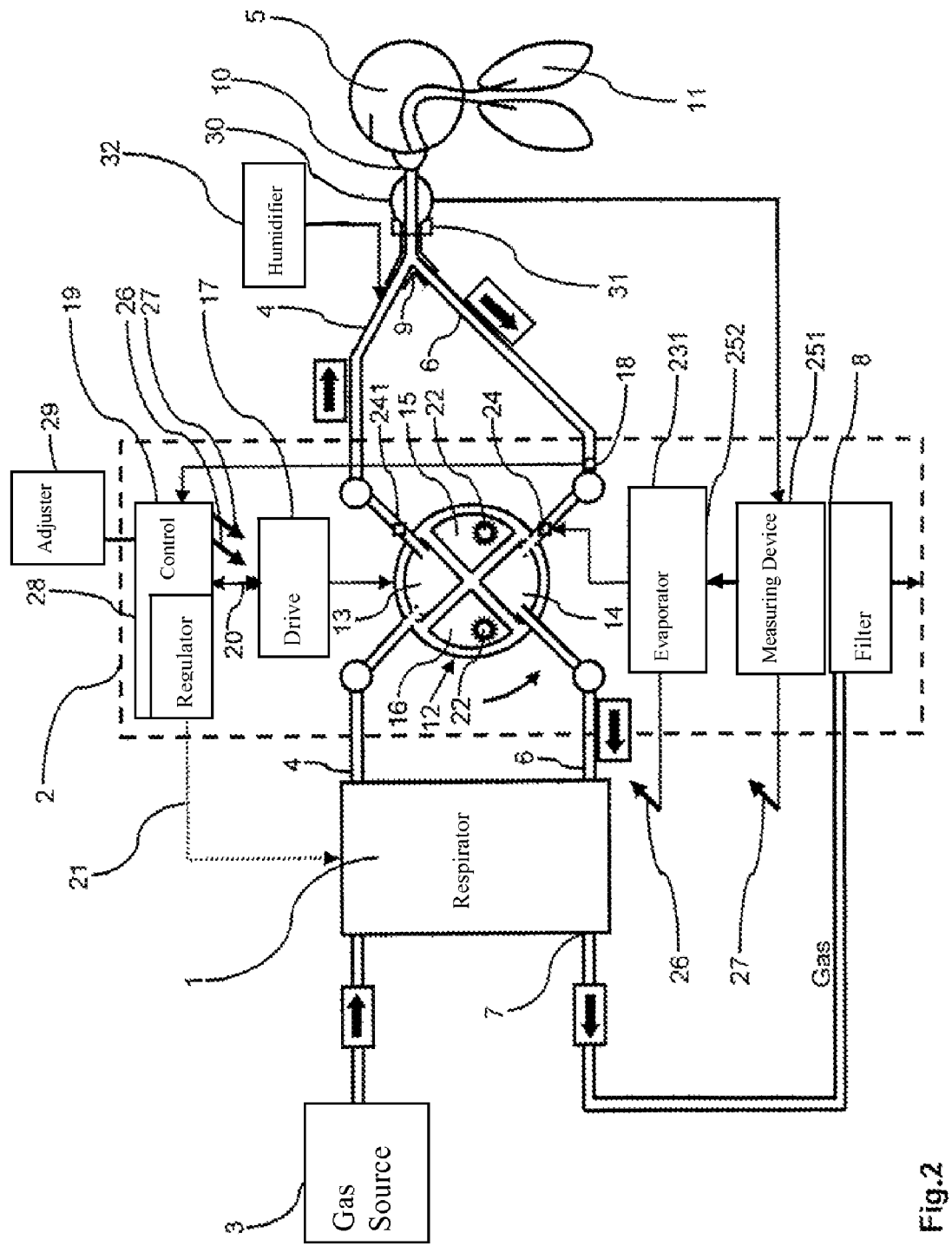
FIG. 2 is a schematic view showing an alternative embodiment to FIG. 1.

FIG. 2 illustrates an alternative embodiment for anesthetic dispensing, in which a suction type anesthetic measuring device 251 is used combined with an anesthetic evaporator 231 operating according to the bypass principle. The breathing gas drawn off at the patient 5 for the gas analysis is sent by means of a return line 252 over an anesthetic evaporator 231 and enriched with anesthetic there. The breathing gas thus conditioned is again introduced into the breathing gas flow at the anesthetic port 24. Identical components are designated by the same reference numbers as in FIG. 1. A loss of gas due to the suction type gas concentration measurement is thus avoided.

Figure 3:
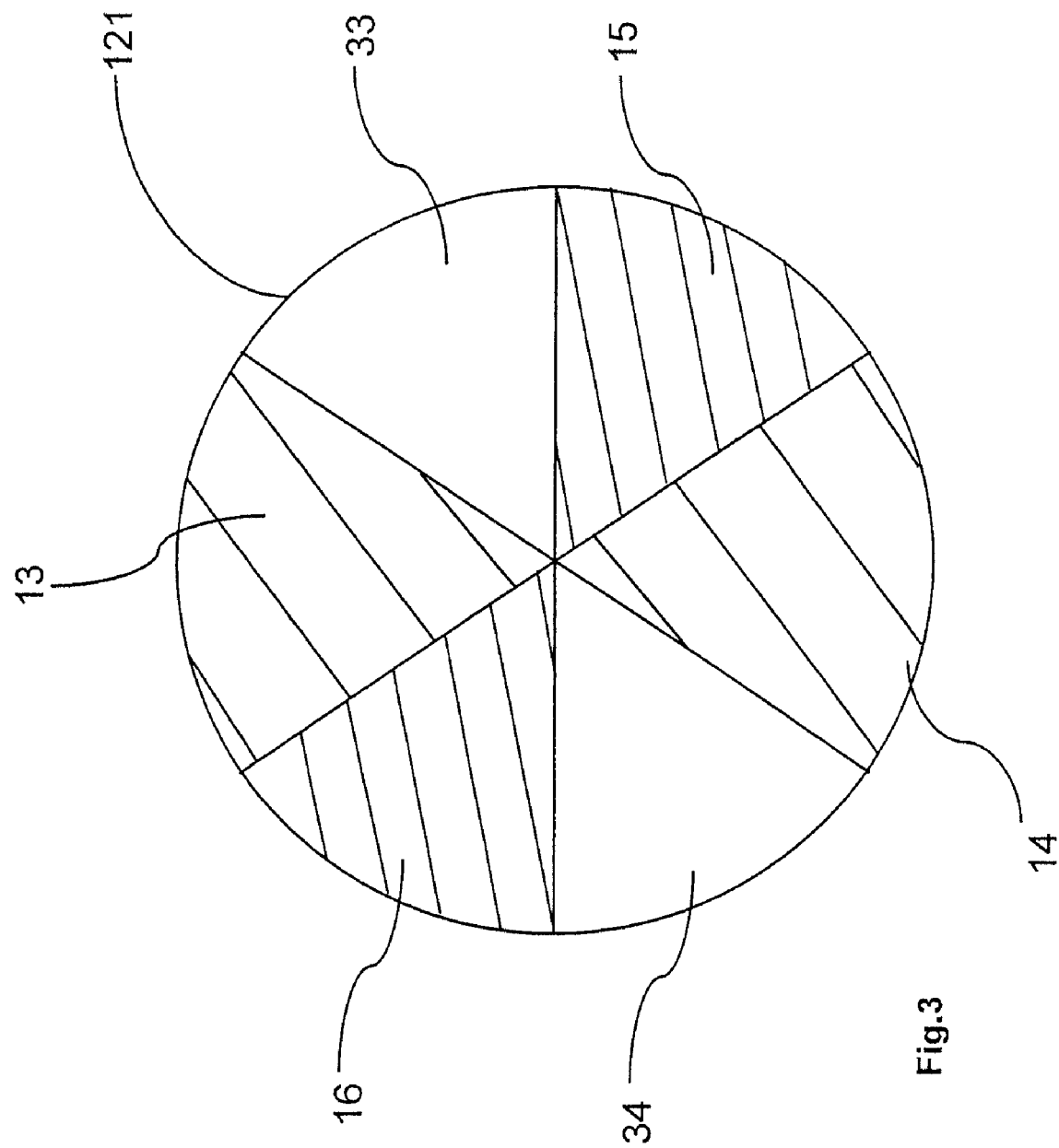
FIG. 3 is a schematic view showing of a filter wheel with empty sectors.

FIG. 3 shows an alternative filter wheel 121 to FIGS. 1 and 2, in which two empty sectors 33, 34, which possess no adsorption or desorption properties and are used simply for passing through gas only, are present besides four adsorption beds 13, 14, 15, 16. The anesthetic can be removed from the breathing gas ducts 4, 6 in a short time by means of the empty sectors 33, 34 when these are arranged in both the inspiration line 4 and in the expiration line 6. The adsorption beds 13, 14, 15, 16 may remain in the original adsorption or desorption state and used again directly, when needed for feeding anesthetics into the breathing gas.

While specific embodiments of the invention have been shown and described in detail to illustrate the application of the principles of the invention, it will be understood that the invention may be embodied otherwise without departing from such principles.

APPENDIX

List of Reference Numbers
1 Respirator
2 Gaseous anesthetic module
3 Pressurized gas source
4 Inspiration line
5 Patient
6 Expiration line
7 Breathing gas outlet
8 Adsorption filter
9 Y-piece
10 Breathing tube
11 Patient's lungs
12, 121 Filter wheel
13, 14,
15, 16 Adsorption bed
17 Drive
18 Breathing phase detector
19 Control unit
20 Data line
21 Signal line
22 UV radiator
23 Anesthetic dispenser
231 Anesthetic evaporator
24, 241 Anesthetic port
25, 251 Anesthetic measuring device
252 Return line
26, 27 Signal line
28 Regulator
29 Set point adjuster
30 Gaseous anesthetic sensor
31 Heat and moisture exchanger
32 Humidifier
33, 34 Empty sector

What is claimed is:

1. A device for adsorbing and desorbing anesthetic, the device comprising:
    an adsorption filter with at least one first adsorption bed and a second adsorption bed;
    an inspiration line and an expiration line between a respirator and a patient, said inspiration line and said expiration line for sending breathing gas through one of said adsorption beds;
    a pivoting means for exposing said first adsorption bed and said second adsorption bed alternatingly to said inspiration line and to said expiration line; and
    an anesthetic dispenser for releasing anesthetic onto one of said first adsorption bed and said second adsorption bed during a period of adsorption, said anesthetic dispenser being connected to said expiration line on an incoming flow side of said adsorption filter.

2. A device in accordance with claim 1, wherein said adsorption filter further comprises, in addition to said adsorption beds, at least one empty sector.

3. A device in accordance with claim 1, further comprising a heating device, which improves desorption of said adsorption beds, is provided in an area of said adsorption filter.

4. A device in accordance with claim 3, wherein said heating device comprises an ultraviolet (UV) radiator.

5. A device in accordance with claim 1, further comprising an anesthetic measuring device in the path of gas of said inspiration line or of said expiration line or in a common gas path of said inspiration line and said expiration line.

6. A device in accordance with claim 1, wherein said anesthetic dispenser comprises a device for releasing liquid or gaseous anesthetic.

7. A device in accordance with claim 5, wherein:
    said anesthetic measuring device is a suction type anesthetic measuring device; and
    said anesthetic dispenser is combined with said suction type anesthetic measuring device providing an anesthetic evaporator.

8. A device in accordance with claim 1, wherein said pivoting means receives synchronization signals, related to breathing phases for pivoting said adsorption beds, via a signal line connected to said respirator.

9. A device in accordance with claim 1, further comprising a breathing phase detector for generating switchover signals for pivoting said pivoting means, said breathing phase detector being arranged in said inspiration line or in said expiration line.

10. A device in accordance with claim 5, further comprising a regulator wherein said anesthetic measuring device is combined with said anesthetic dispenser and with a regulator and each of said anesthetic measuring device, said anesthetic dispenser and said regulator are components of a control circuit for setting a preset anesthetic concentration.

11. A device in accordance with claim 1, wherein said adsorption beds comprise carbon fiber mats.

12. A device in accordance with claim 1, wherein said anesthetic dispenser is designed for at least temporarily being connected to said inspiration line, wherein an anesthetic concentration of said breathing gas provided to the patient is increased with said anesthetic dispenser at least temporarily connected to said inspiration line.

13. An anesthetic system comprising:
    a respirator;
    an adsorption filter with at least one first adsorption bed and a second adsorption bed;
    a patient connection with an inspiration line and an expiration line between said respirator and a patient, said inspiration line and said expiration line for sending breathing gas through one of said adsorption beds;

a pivoting means for exposing said first adsorption bed and said second adsorption bed alternatingly to said inspiration line and to said expiration line; and an anesthetic dispenser for releasing anesthetic onto at least one of said first adsorption bed and said second adsorption bed during a period of adsorption, said anesthetic dispenser being connected to said expiration line on an incoming flow side of said adsorption filter.

14. An anesthetic system in accordance with claim 13, wherein said adsorption filter further comprises, in addition to said adsorption beds, at least one empty sector.

15. An anesthetic system in accordance with claim 13, further comprising a heating device, which improves desorption of said adsorption beds, is provided in an area of said adsorption filter.

16. An anesthetic system in accordance with claim 13, further comprising an anesthetic measuring device in the path of gas of said inspiration line or of said expiration line or in a common gas path of said inspiration line and said expiration line, wherein:
    said anesthetic measuring device is a suction type anesthetic measuring device; and
    said anesthetic dispenser is combined with said suction type anesthetic measuring device providing an anesthetic evaporator.

17. An anesthetic system in accordance with claim 13, wherein said pivoting means receives synchronization signals, related to breathing phases for pivoting said adsorption beds, via a signal line connected to said respirator or from a breathing phase detector for generating switchover signals for pivoting said pivoting means, said breathing phase detector being arranged in said inspiration line or in said expiration line.

18. An anesthetic system in accordance with claim 14, further comprising:
    an anesthetic measuring device in the path of gas of said inspiration line or of said expiration line or in a common gas path of said inspiration line and said expiration line; and
    a regulator wherein said anesthetic measuring device combined with said anesthetic dispenser and said regulator form a control circuit for setting a preset anesthetic concentration.

19. An anesthetic system in accordance with claim 13, wherein said anesthetic dispenser is at least temporarily connected to said inspiration line, said breathing gas comprising an inspired gas, wherein said inspired gas is provided with an increased anesthetic concentration with said anesthetic dispenser at least temporarily connected to said inspiration line, said inspired gas with said increased anesthetic concentration being delivered to the patient.

20. A device for adsorbing and desorbing anesthetic, the device comprising:
    an adsorption filter with at least one first adsorption bed and a second adsorption bed;
    an inspiration line and an expiration line between a respirator and a patient, said inspiration line and said expiration line for sending breathing gas through one of said adsorption beds;
    a pivoting means for exposing said first adsorption bed and said second adsorption bed alternatingly to said inspiration line and to said expiration line; and
    an anesthetic dispenser for releasing anesthetic onto one of said first adsorption bed and said second adsorption bed during a period of adsorption, said anesthetic dispenser being connected to said expiration line on an incoming flow side of said adsorption filter, said anesthetic dispenser being designed for at least temporarily being connected to said inspiration line, wherein a switch over of said anesthetic dispenser to said inspiration line builds up a high anesthetic concentration in the breathing gas inspired by the patient.

* * * * *